US00PP19667P2

(12) United States Plant Patent
Larsen

(10) Patent No.: US PP19,667 P2
(45) Date of Patent: Feb. 3, 2009

(54) *OSTEOSPERMUM* PLANT NAMED 'SUNNY EVITA'

(50) Latin Name: *Osteospermum ecklonis*
Varietal Denomination: Sunny Evita

(75) Inventor: Bjarne Nyholm Larsen, Odense N. (DK)

(73) Assignee: Sunny Gronnegyden APS, Odense (DE)

( * ) Notice: Subject to any disclaimer, the term of this patent is extended or adjusted under 35 U.S.C. 154(b) by 0 days.

(21) Appl. No.: 11/983,729

(22) Filed: Nov. 12, 2007

(51) Int. Cl.
*A01H 5/00* (2006.01)

(52) U.S. Cl. ..... Plt./360
(58) Field of Classification Search ..... Plt./360
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Osteospermum* plant named 'Sunny Evita', characterized by its compact and mounded plant habit; freely branching growth habit; freely flowering habit; daisy-type inflorescences with oblanceolate-shaped ray florets that are light purple in color; and have good garden performance.

1 Drawing Sheet

Botanical designation: *Osteospermum ecklonis.*
Cultivar denomination: 'Sunny Evita'.

CROSS-REFERENCED TO RELATED APPLICATIONS

Applicant: Bjarne Nyholm Larsen.

Title: *Osteospermum* Plant Named 'Sunny Xandra'.

Filed: U.S. Plant patent application No. 11/983,728 Filed Concurrently.

BACKGROUND OF THE INVENTION

The present invention relates to a new and distinct cultivar of *Osteospermum* plant, botanically known as *Osteospermum ecklonis,* and hereinafter referred to by the name 'Sunny Evita'.

The new *Osteospermum* is a product of a planned breeding program conducted by the Inventor in Odense, Denmark. The objective of the program is to create and develop new *Osteospermum* cultivars with compact and uniformly mounded plant habit, freely flowering habit and attractive inflorescence coloration.

The new *Osteospermum* originated from a cross-pollination by the Inventor in May, 2004 of the *Osteospermum ecklonis* cultivar Sunny Serena, disclosed in U.S. Plant Pat. No. 15,693, as the female, or seed, parent with a proprietary selection of *Osteospermum ecklonis* identified as code number 10.501.02, not patented, as the male, or pollen, parent. The new *Osteospermum* was discovered and selected by the Inventor as a single flowering plant within the progeny of the stated cross-pollination in a controlled environment in Odense, Denmark in June, 2005.

Asexual reproduction of the new *Osteospermum* by terminal cuttings in a controlled environment in Odense, Denmark since January, 2007, has shown that the unique features of this new *Osteospermum* are stable and reproduced true to type in successive generations.

SUMMARY OF THE INVENTION

The cultivar Sunny Evita has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunny Evita'. These characteristics in combination distinguish 'Sunny Evita' as a new and distinct cultivar of *Osteospermum:*

1. Compact and mounded plant habit.
2. Freely branching growth habit.
3. Freely flowering habit.
4. Daisy-type inflorescences with oblanceolate-shaped ray florets that are light purple in color.
5. Good garden performance.

Plants of the new *Osteospermum* differ from plants of the female parent, the cultivar Sunny Serena, primarily in ray floret color as plants of the cultivar Sunny Serena have salmon-colored ray florets.

Plants of the new *Osteospermum* differ from plants of the male parent selection primarily in ray floret color as plants of the male parent selection have white-colored ray florets.

Plants of the new *Osteospermum* differ from plants of the *Osteospermum* cultivar Sunny Xandra, disclosed in a U.S. Plant patent application filed concurrently, primarily in ray floret coloration.

Plants of the new *Osteospermum* can be compared to plants of the *Osteospermum* cultivar Sunny Fiona, disclosed in U.S. Plant patent application Ser. No. 11/821,112. In side-by-side comparisons conducted in Odense, Denmark, plants of the new *Osteospermum* differed primarily from plants of the cultivar Sunny Fiona in ray floret color as ray florets of plants of the cultivar Sunny Fiona are deep pink in color.

BRIEF DESCRIPTION OF THE PHOTOGRAPHS

The accompanying photographs illustrate the overall appearance of the new *Osteospermum.* This photographs shows the colors as true as it is reasonably possible to obtain in colored reproductions of this type. Colors in the photographs may differ slightly from the color values cited in the detailed botanical description which accurately describe the colors of the new *Osteospermum*.

The photograph at the top of the sheet comprises a side perspective view of a typical flowering plant of 'Sunny Evita'.

The photograph at the bottom of the sheet is a close-up view of a typical inflorescence of 'Sunny Evita'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in Odense, Denmark during the spring in a glass-covered greenhouse and under conditions and practices which approximate those generally used in commercial *Osteospermum* production. During the production of the plants, day temperatures ranged from 14° C. to 20° C., night temperatures averaged 14° C. and light levels ranged from 200 to 800 watts per square meter. Measurements and numerical values represent averages for typical flowering plants. Plants were pinched one time and were about 15 weeks old when the photographs and description were taken.

Botanical classification: *Osteospermum ecklonis* cultivar Sunny Evita.

Parentage:

*Female, or seed, parent.*—*Osteospermum ecklonis* cultivar Sunny Serena, disclosed in U.S. Plant Pat. No. 15,693.

*Male, or pollen, parent.*—Proprietary selection of *Osteospermum ecklonis* identified as code number 10.501.02, not patented.

Propagation:

*Type.*—Terminal vegetative cuttings.

*Time to initiate roots, summer.*—About ten days at 18° C.

*Time to initiate roots, winter.*—About twelve days at 18° C. to 20° C.

*Time to produce a rooted cutting, summer.*—About three weeks at 18° C. to 20° C.

*Time to produce a rooted cutting, winter.*—About four weeks at 18° C.

*Root description.*—Medium in thickness, fibrous; white in color.

*Rooting habit.*—Freely branching; moderately dense.

Plant description:

*Plant form/growth habit.*—Compact and mounded plant habit. Inflorescences positioned above and beyond the foliar plane. Low to moderately vigorous growth habit.

*Plant height.*—About 23.3 cm.

*Plant diameter.*—About 19.5 cm.

*Lateral branches.*—Quantity per plant: Freely branching, about five primary lateral branches per plant. Length: About 12.6 cm. Diameter: About 4 mm. Internode length: About 7 mm. Strength: Strong. Texture: Sparsely pubescent. Color: 144B.

*Foliage description.*—Arrangement: Alternate, simple; sessile. Length: About 5.2 cm. Width: About 2.4 cm. Shape: Obovate to spatulate. Apex: Rounded to broadly acute. Base: Cuneate. Margin: Dentate; coarse, irregular. Texture, upper and lower surface: Smooth, glabrous; leathery; moderately dense pubescence along the leaf margins. Venation pattern: Pinnate. Color: Developing foliage, upper surface: 143A. Developing foliage, lower surface: 143C. Fully expanded foliage, upper surface: 137A; venation, 138B. Fully expanded foliage, lower surface: 137B; venation, 144B.

Inflorescence description:

*Appearance.*—Daisy-type inflorescence form with oblanceolate-shaped ray florets. Inflorescences positioned above and beyond the foliage; inflorescences terminal and axillary. Disc and ray florets developing acropetally on a capitulum. Inflorescences face mostly upright to outward. Freely flowering habit; about 25 inflorescences develop per plant. Inflorescences not persistent. Inflorescences not fragrant.

*Flowering response.*—In northern Europe, plants of the new *Osteospermum* flower continuously from spring to late summer. Early flowering habit, plants begin flowering about eight weeks after pinching. Inflorescences last about two weeks on the plant.

*Inflorescence bud.*—Height: About 1.5 cm. Diameter: About 1.1 cm. Shape: Ovate. Color: 143A; towards the apex, between N144B and 151C.

*Inflorescence size.*—Diameter: About 6.1 cm. Depth (height): About 1.5 cm. Disc diameter: About 4 mm. Receptacle diameter: About 1.4 mm. Receptacle height: About 6 mm.

*Ray florets.*—Length: About 3 cm. Width: About 8.5 mm. Shape: Oblanceolate. Apex: Retuse. Base: Attenuate. Margin: Entire. Texture: Smooth, glabrous; at the base, pubescent. Number of ray florets per inflorescence: About 17 in about two whorls. Color: When opening, upper surface: 76B; towards the base, slightly darker than 76B. When opening, lower surface: 4C; venation 4B. Fully opened, upper surface: 76B to 76C; towards the base, slightly darker than 76B. With development, color becoming closer to 77B to 77C; towards the base, slightly lighter than 83D. Fully opened, lower surface: 4D; venation, slightly darker than 4B to 4C.

*Disc florets.*—Shape: Tubular; apex dentate, five-pointed. Length: About 8 mm. Diameter, apex: About 2.5 mm. Diameter, base: About 1 mm. Number of disc florets per inflorescence: About 50. Color: Immature: Close to 145D. Mature: Apex, 122C; mid-section and base, 155C.

*Phyllaries.*—Quantity per inflorescence: About 16 in a single whorl. Length: About 9 mm. Width: About 1.5 mm. Shape: Lanceolate. Apex: Acuminate, elongated. Base: Cuneate. Margin: Entire. Texture, upper and lower surfaces: Sparsely pubescent. Color, upper surface: 138B to 138C. Color, lower surface: 143A to 143C; towards the margins, 143C.

*Peduncles.*—Length, terminal peduncle: About 5.7 cm. Length, fourth peduncle: About 6.6 cm. Diameter: About 2 mm. Strength: Strong. Aspect, terminal peduncles: Mostly upright. Aspect, axillary peduncles: About 25° from vertical. Texture: Sparsely pubescent. Color: 144A.

*Reproductive organs.*—Androecium: Present on disc florets only. Anther shape: Lanceolate. Anther length: About 2 mm. Anther color: Close to 202A. Pollen amount: Moderate. Pollen color: 21A. Gynoecium: Present on both ray and disc florets. Pistil length: About 5 mm. Stigma shape: Lanceolate. Stigma color: 200A to 200B. Style length: About 4 mm. Style color: 150D. Ovary color: 145A.

*Seeds/fruits.*—Seed and fruit development have not been observed on plants of the new *Osteospermum.*

Disease/pest resistance: Plants of the new *Osteospermum* have not been shown to be resistant to pathogens and pests common to *Osteospermums.*

Garden performance: Plants of the new *Osteospermum* have been observed to have good garden performance and to tolerate rain, wind and temperatures ranging from about 0° C. to about 40° C.

It is claimed:

1. A new and distinct *Osteospermum* plant named 'Sunny Evita' as illustrated and described.

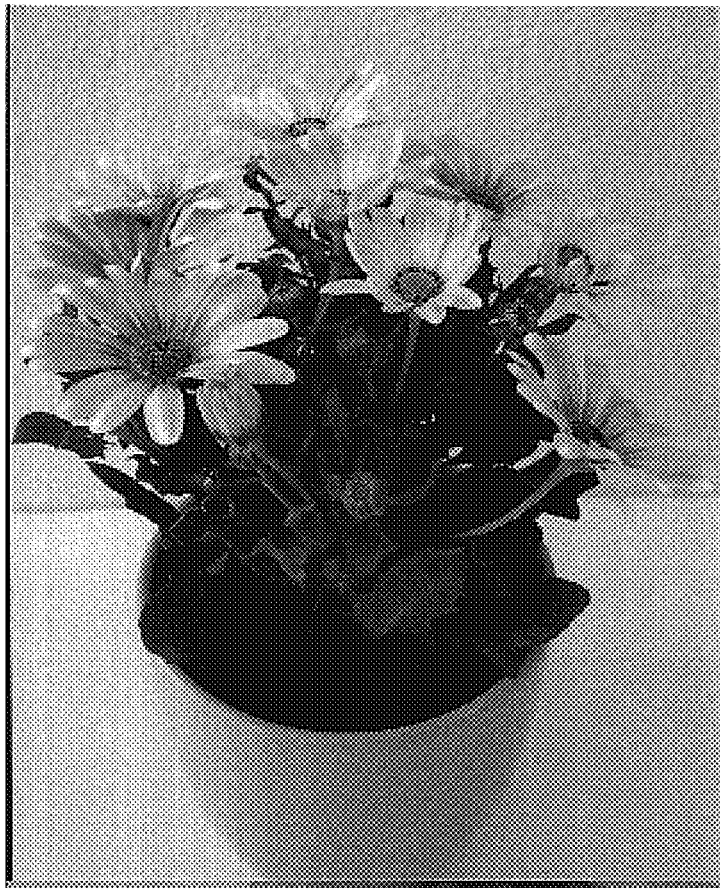
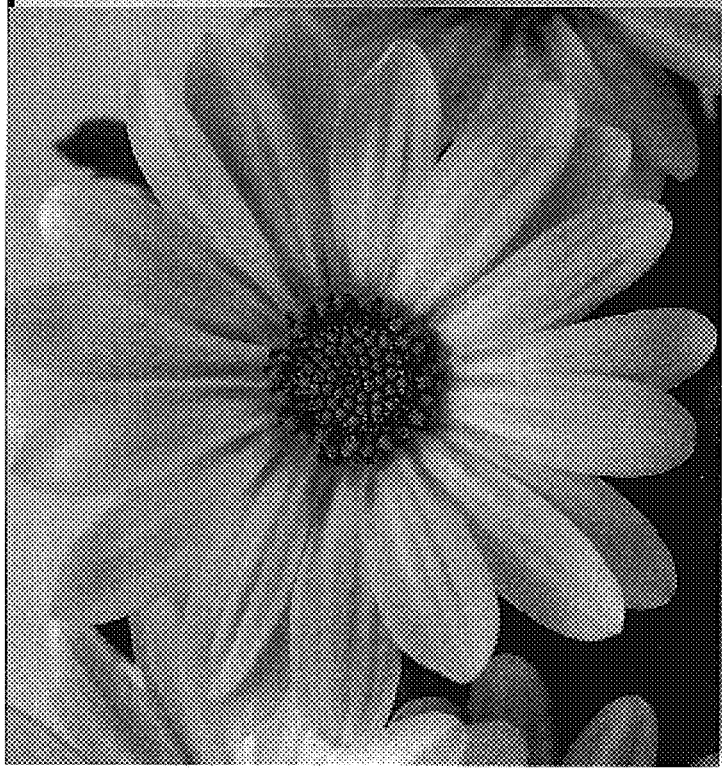

* * * * *